(12) United States Patent
Ainsworth et al.

(10) Patent No.: US 8,940,038 B2
(45) Date of Patent: Jan. 27, 2015

(54) LOW PROFILE STENT WITH FLEXIBLE LINK

(71) Applicant: Abbott Cardiovascular Systems Inc., Santa Clara, CA (US)

(72) Inventors: Stephen D. Ainsworth, Los Gatos, CA (US); Andreina P. Gomez, Santa Clara, CA (US)

(73) Assignee: Abbott Cardiovascular Systems Inc.

( * ) Notice: Subject to any disclaimer, the term of this patent is extended or adjusted under 35 U.S.C. 154(b) by 0 days.

(21) Appl. No.: 13/782,302

(22) Filed: Mar. 1, 2013

(65) Prior Publication Data

US 2013/0178927 A1 Jul. 11, 2013

Related U.S. Application Data

(62) Division of application No. 12/400,079, filed on Mar. 9, 2009, now Pat. No. 8,388,675, which is a division of application No. 09/894,984, filed on Jun. 28, 2001, now Pat. No. 7,520,892.

(51) Int. Cl.
*A61F 2/82* (2013.01)
*A61F 2/89* (2013.01)
*A61F 2/91* (2013.01)
*A61F 2/915* (2013.01)

(52) U.S. Cl.
CPC ... *A61F 2/89* (2013.01); *A61F 2/91* (2013.01); *A61F 2/915* (2013.01); *A61F 2002/91508* (2013.01); *A61F 2002/91575* (2013.01); *A61F 2230/0054* (2013.01)
USPC ......................................... 623/1.16; 623/1.15

(58) Field of Classification Search
CPC ............. A61F 2/82; A61F 2/86; A61F 2/825; A61F 2/89; A61F 2002/91508; A61F 2002/91516; A61F 2002/91525; A61F 2002/91566; A61F 2002/91558; A61F 2002/91575
USPC ....................................... 623/1.15, 1.16, 1.17
See application file for complete search history.

(56) References Cited

U.S. PATENT DOCUMENTS

| 5,911,754 | A  | * | 6/1999 | Kanesaka et al. ............ 623/1.15 |
| 5,925,061 | A  |   | 7/1999 | Ogi et al. |
| 6,066,169 | A  | * | 5/2000 | McGuinness ................ 623/1.16 |
| 6,190,403 | B1 |   | 2/2001 | Fischell et al. |
| 6,245,101 | B1 |   | 6/2001 | Drasler et al. |
| 6,264,688 | B1 |   | 7/2001 | Herklotz et al. |
| 6,416,543 | B1 | * | 7/2002 | Hilaire et al. ................ 623/1.16 |
| 6,629,994 | B2 |   | 10/2003 | Gomez et al. |
| 6,790,227 | B2 |   | 9/2004 | Burgermeister |
| 2002/0058989 | A1 |   | 5/2002 | Chen et al. |
| 2002/0123792 | A1 | * | 9/2002 | Burgermeister ............. 623/1.15 |

FOREIGN PATENT DOCUMENTS

WO WO98/30173 * 7/1998 ............ A61F 2/06

* cited by examiner

*Primary Examiner* — David Isabella
*Assistant Examiner* — Suba Ganesan
(74) *Attorney, Agent, or Firm* — Fulwider Patton LLP

(57) ABSTRACT

The invention provides an improved stent design for repairing vasculature, the stent having rings including struts defining first peaks and second peaks, selected second peaks of adjacent rings being connected by links. The stent design incorporates non-linear links with undulating portions extending generally perpendicular to or circumferentially with respect to a longitudinal axis of the stent and adjacent first peaks with different longitudinal lengths such that stent flexibility is increased without sacrificing stent compression for delivery.

12 Claims, 6 Drawing Sheets

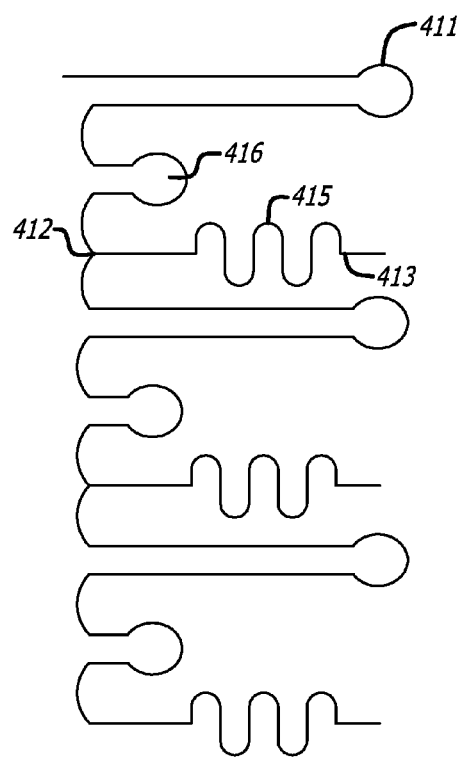
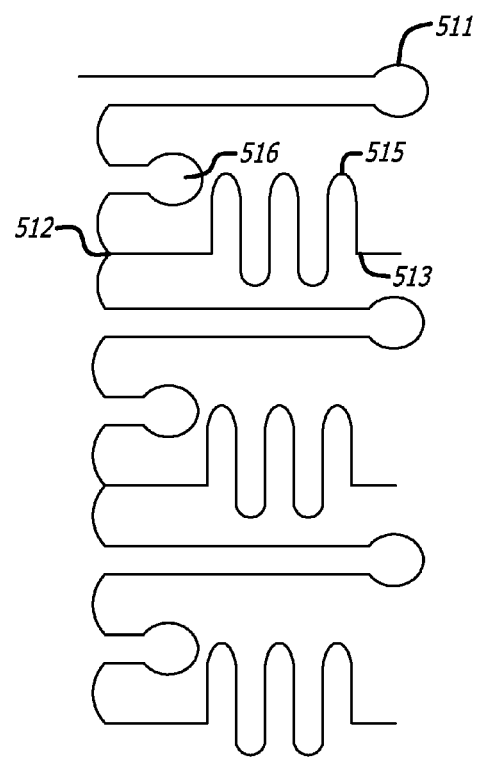
FIG. 4C
FIG. 4D

LOW PROFILE STENT WITH FLEXIBLE LINK

This application is a division of U.S. Ser. No. 12/400,079, filed Mar. 9, 2009, which is a division of U.S. Ser. No. 09/894,984 filed Jun. 28, 2001 now U.S. Pat. No. 7,520,892 both of which are incorporated by reference in their entirety.

BACKGROUND OF THE INVENTION

The invention relates generally to a device for repairing body lumens and more particularly, to a design for stents that provides desired flexibility while still allowing the stent to be crimped to a small profile for delivery to the implant site.

Stents conventionally repair blood vessels that are diseased. Stents are generally hollow and cylindrical in shape and have terminal ends that are generally perpendicular to their longitudinal axis. In use, the conventional stent is positioned at the diseased area of a vessel and, after deployment, the stent provides an unobstructed pathway for blood flow.

Repair of vessels that are diseased can be particularly challenging since the stent must be precisely positioned, provide adequate coverage of the disease and maintain vessel patency in order to allow adequate blood flow. Therefore, the stent must provide adequate coverage to the diseased portion of the vessel, without compromising blood flow, and extend to a point within and beyond the diseased portion. Unopposed stent elements may promote lumen compromise during neointimal formation and healing, producing restenosis and requiring further procedures. Moreover, by extending into the vessel lumen at a bifurcation, the stent may block access for further interventional procedures.

Recently, the art has taught the use of stents having a cylindrical body with rings aligned along a longitudinal axis, where each ring has a delivered diameter in which it is crimped or compressed tightly onto a catheter, and an implanted diameter where the stent is implanted in a vessel. Each ring includes a number of first peaks and one or more second peaks, with at least one second peak of each ring connected to a second peak of the adjacent ring by a link, the rings and links being made of struts. The first peaks are configured to spread apart to permit the rings to be expanded outwardly or to be compressed radially inwardly onto a balloon portion of a delivery catheter. The second peaks and links provide longitudinal connection points between the rings.

By varying the number of rings and first peaks, the outward expansion of the various sections of the implanted stent can be customized and, thereby providing additional support provided at selected areas of the patient's lumen. Moreover, by varying the length and shapes of the links which connect the rings, the expandability, flexibility and degree of compression attainable may be varied. Flexibility of a stent is important with regard to both the ability of the stent to conform to the curvature of a tortuous artery after expansion and to the ability to maneuver the compressed stent through anatomy for delivery to the implant site. In particular, non-linear links may have undulating portions which are directed generally perpendicular to a longitudinal axis of the stent and which act as a hinge to enhance stent flexibility. Although the undulating portions provide desired stent flexibility, they also limit the extent of compression that may be achieved in the stent and therefore, result in increasing the delivery profile. Because the undulating portions extend perpendicular to the axis of the stent, in certain designs, they will contact the adjacent first peaks when the stent is compressed, thereby limiting the degree of compression achievable.

It may therefore be desirable for a stent to embody structure which not only provides additional support to a body lumen but also permits the stent to be compressed radially to a relatively high degree while maintaining necessary flexibility. Such a stent would be capable of being delivered through tortuous vasculature as well as being well suited for treating disease. The present invention endeavors to satisfy these needs.

SUMMARY OF THE INVENTION

The invention provides an improved ring design for cylindrical stents used to repair a vessel. Stents embodying the improved ring design are contemplated to provide required support in the repair of vasculature as well as to include structure providing the stent with desired flexibility and crimpability.

In one aspect, the stent of the present invention has rings with first peaks and second peaks, the second peaks of longitudinally adjacent rings being connected by links. The stent design of the present invention incorporates non-linear links and rings with first peaks defined by struts having different lengths or otherwise occupying staggered longitudinal positions along the stent, such structure being configured such that desired stent flexibility is achieved without sacrificing stent compression for delivery.

In another aspect, the stent of the present invention includes rings aligned along a longitudinal axis, where each ring has a first diameter in which it is crimped or compressed tightly, and a second diameter when the stent is implanted in a vessel. Each ring includes a number of first peaks and one or more second peaks, with at least one second peak of each ring connected to a second peak of a longitudinally adjacent ring by a link. The first peaks are configured to spread apart to permit the rings to be expanded outwardly or to be compressed radially inwardly onto a delivery catheter.

Additionally, at least some of the links which connect the second peaks are non-linear and have struts defining undulating portions, the struts being generally perpendicular to a longitudinal axis of the stent. These undulating portions act to enhance stent flexibility as well as vessel coverage. Furthermore, struts defining certain of the first peaks immediately adjacent each non-linear link have different lengths. The different lengths of these first peaks allow the undulating portions to be imbedded or nested within a ring width and thereby facilitate greater compression of the stent for delivery.

In one embodiment, struts defining one of the first peaks adjacent to each undulating link are shortened. The resulting space in the ring accommodates about one half of a perpendicular or circumferentially extending portion as well as a longitudinal length of the undulating link, thereby facilitating greater compression of the stent.

In an alternate embodiment, struts defining one of the first peaks adjacent to each undulating link is shortened and struts defining the other first peak adjacent each undulating link is lengthened. Lengthening the struts of the adjacent first peaks provides additional space to accommodate the entire generally perpendicular or circumferentially extending portion of the undulating link with a smaller decrease in the unsupported surface area of the expanded stent. Moreover, the lengthened first peaks may be adapted to facilitate accommodating undulating portions with additional perpendicular or circumferentially extending transitions.

In another alternate embodiment, the generally perpendicular transitions of the undulating portions are asymmetrical, the transitions longer in the direction of a shortened first peak. The longer perpendicular transitions can be adapted to customize the flexibility of the stent.

In yet another alternate embodiment, not all the links in each ring have undulating portions, with only the struts of certain of the adjacent first peaks being shortened. Selective placement of the undulating links allows the flexibility of portions of the stent to be tailored to the vessel in which it is implanted.

The basic concept of the ring design of the present invention may be incorporated into stents having various link shapes and lengths as well as stents having sections with different link configurations. It is contemplated that the ring design of the present invention may be applied whenever it is desired to increase the flexibility of a stent while maintaining desired crimpability, by incorporating undulating portions into the links and embedding or nesting the links within stent rings.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 4C is a schematic view of an embodiment of the ring design of the present invention in which each undulating link has three perpendicular transitions;

FIG. 4D is a schematic view of an embodiment of the ring design of the present invention in which the perpendicular transitions of each undulating link are asymmetrical.

DETAILED DESCRIPTION OF THE PREFERRED EMBODIMENTS

Figure 1A:
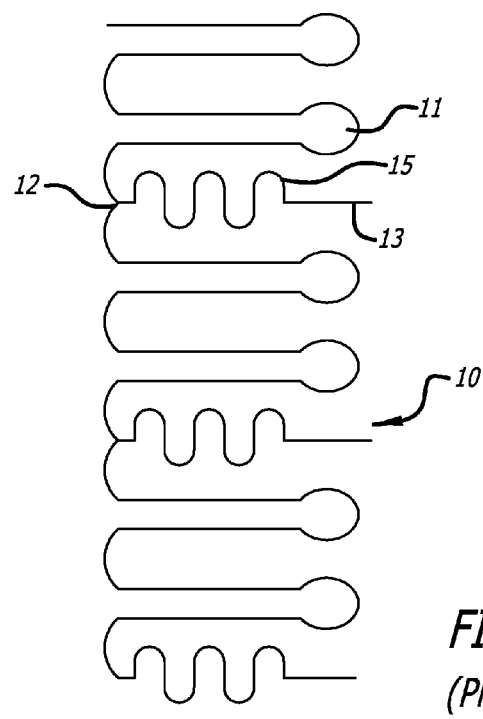
FIG. 1A is a schematic view of a prior art ring design in which every link has an undulating portion.
Figure 1B:
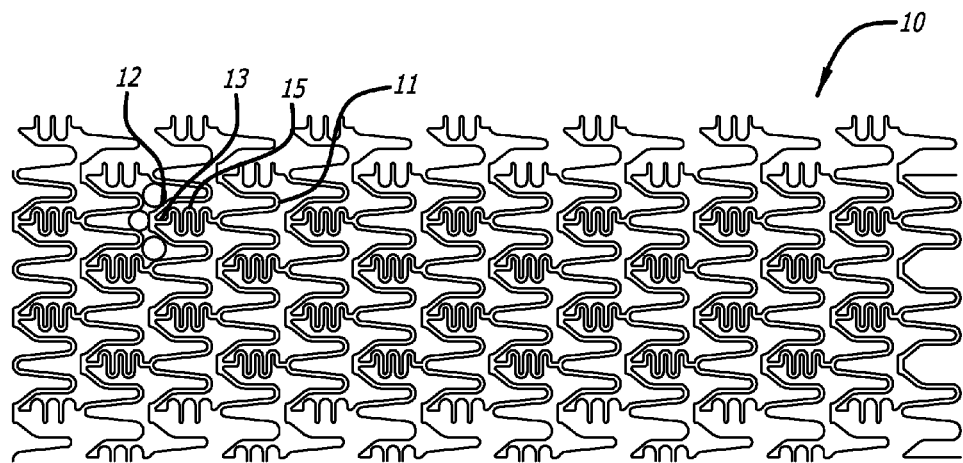
FIG. 1B is a flattened elevation view depicting a prior art stent in which every link has an undulating portion.
Figure 2A:
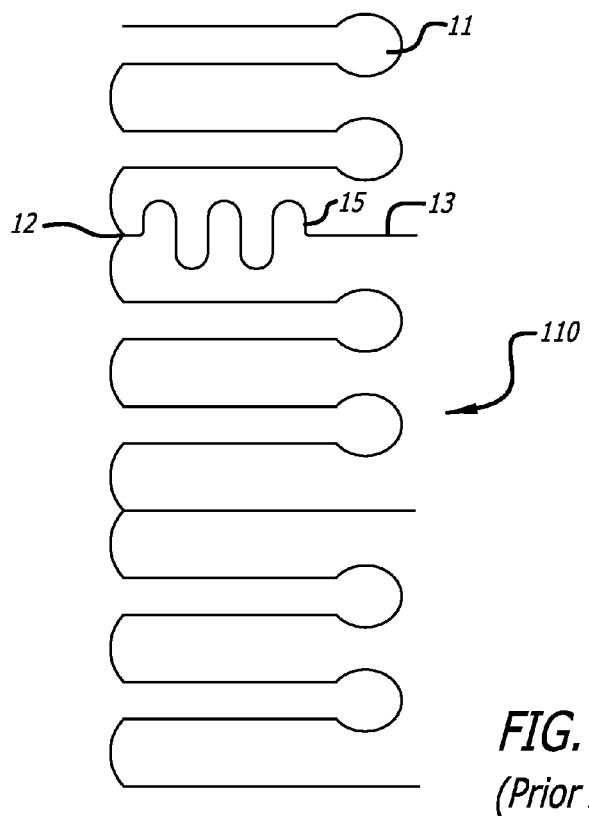
FIG. 2A is a schematic view of a prior art ring design in which not all the links have an undulating portion.
Figure 2B:
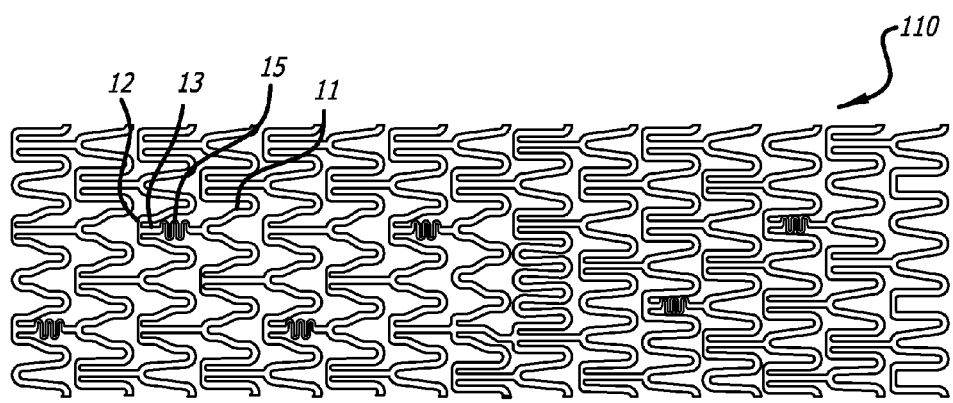
FIG. 2B is a flattened elevation view depicting a prior art stent in which not all the links have an undulating portion.

The stent ring design of the present invention incorporates non-linear links with undulating portions extending generally perpendicularly or circumferentially with respect to a longitudinal axis of the stent and adjacent first peaks certain of which are defined by struts with different lengths such that stent flexibility is enhanced without sacrificing stent compression for delivery. Prior art attempts at increasing the flexibility of stents by incorporating undulating portions in the links have been developed. For example, FIGS. 1 and 2 depict prior stents which include undulating portions in links that connect longitudinally arranged rings characterized by having first 11 and second 12 peaks. FIGS. 1A and 1B depict a stent 10 having an undulating portion 15 in each link 13 between second peaks 12. FIGS. 2A and 2B depict a stent 110 in which only certain selected links 13 between second peaks 12 have an undulating portion 15. Note that each first peak 14 of a selected ring terminates at the same longitudinal position along the stent 10, 110. Note also that the undulating portions 15 are generally perpendicular to a longitudinal axis of the stent 10, 110 and, therefore, occupy a space that is wider than a cross-section of an individual link 13. The undulating portions 15 provide the stent with desired flexibility. However, the undulating portions 15 can interfere with the adjacent first peaks 11 when the stent is compressed for delivery, thereby decreasing the degree of compressibility achievable.

The stent ring design of the present invention incorporates non-linear links with undulating portions extending generally perpendicularly or circumferentially with respect to a longitudinal axis of the stent and adjacent first peaks certain of which are defined by struts with different lengths such that stent flexibility is enhanced without sacrificing stent compression for delivery. Prior art attempts at increasing the flexibility of stents by incorporating undulating portions in the links have been developed. For example, FIGS. 1 and 2 depict prior stents which include undulating portions in links that connect longitudinally arranged rings characterized by having first 11 and second 12 peaks. FIGS. 1A and 1B depict a stent 10 having an undulating portion 15 in each link 13 between second peaks 12. FIGS. 2A and 2B depict a stent 110 in which only certain selected links 13 between second peaks 12 have an undulating portion 15. Note that each first peak 14 of a selected ring terminates at the same longitudinal position along the stent 10, 110. Note also that the undulating portions 15 are generally perpendicular to a longitudinal axis of the stent 10, 110 and, therefore, occupy a space that is wider than a cross-section of an individual link 13. The undulating portions 15 provide the stent with desired flexibility. However, the undulating portions 15 can interfere with the adjacent first peaks 11 when the stent is compressed for delivery, thereby decreasing the degree of compressibility achievable.

Referring to FIGS. 3A-C and 4A-E, the stent of the present invention is shown. The design of the stent of the present invention provides the flexibility desired as well as enhances compressibility. By incorporating first peaks a selection of which being defined by struts having different lengths, the undulating portion of the links can be embedded or nested within a ring of the stent when placed in a compressed configuration.

Figure 3A:
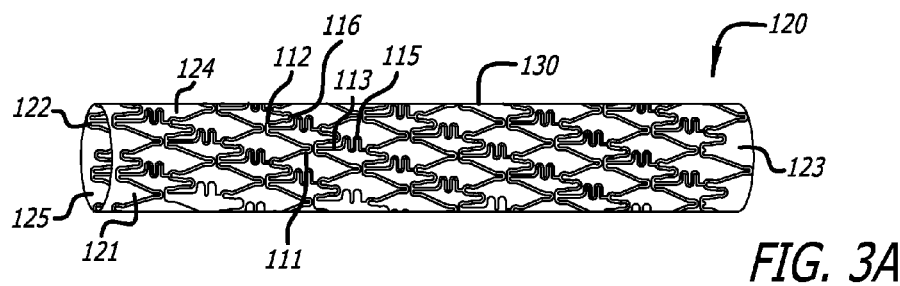
FIG. 3A is a perspective view depicting a preferred embodiment of the stent of the present invention in an unexpanded configuration.
Figure 3B:
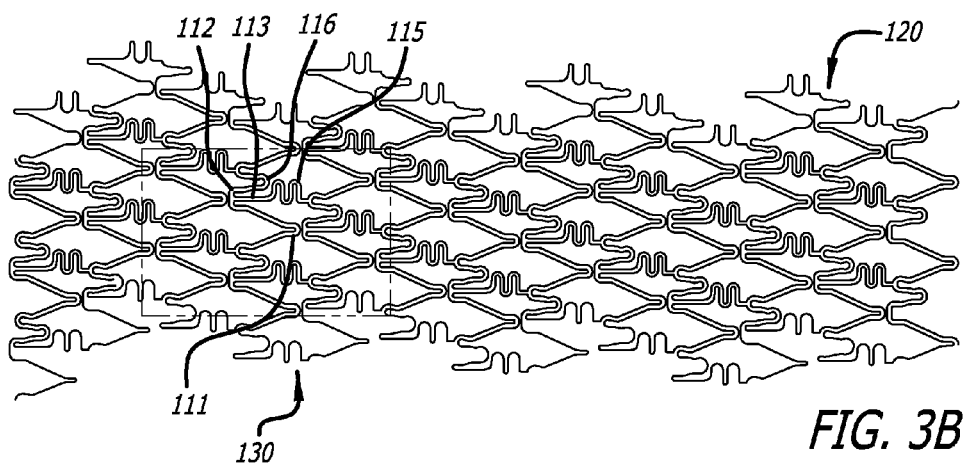
FIG. 3B is a flattened elevation view depicting a preferred embodiment of the stent of the present invention.
Figure 3C:
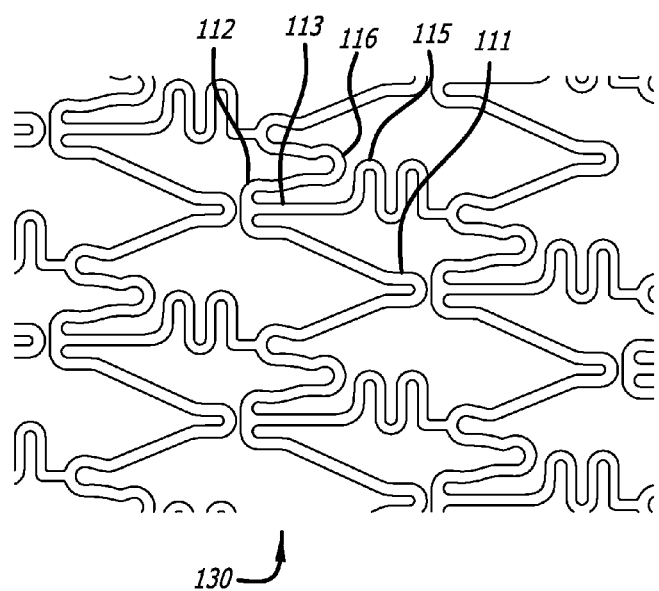
FIG. 3C is a an enlarged view of the portion of the stent in FIG. 3B indicated by the dotted line.

With reference to FIGS. 3A-C there is shown a preferred embodiment of the present invention. The depicted stent 120 has a cylindrical body 121 that includes a proximal end 122 and a distal end 123. The stent 120 has an outer surface 124 which contacts vasculature or other body lumens into which it is placed when implanted and an inner surface 125 which accommodates blood flow. The stent 120 can be described as having a plurality of connected rings 130 aligned along a common longitudinal axis of the stent 120. In one aspect, each ring 130 embodies struts defining a generally serpentine pattern of alternating peaks. As such, each ring 130 includes a plurality of first peaks directed in a first longitudinal direction and a plurality of second peaks directed in a second, opposite longitudinal direction. In one preferred embodiment, a ring 130 has six second peaks 112 and has six first peaks defined by struts of various lengths thereby creating three long first peaks 111 and three short first peaks 116. The struts of the first peaks 111, 116 are configured to be spread apart to permit the stent 120 to be expanded to a larger diameter or compressed tightly toward each other to a smaller diameter for placement onto a catheter. The alignment of any two adjacent rings 130 is such that only three second peaks 112 of adjacent rings 130 are aligned or in phase. The aligned second peaks 112 of adjacent rings 130 are connected by a link 113.

Each link 113 between second peaks 112 is further defined by an undulating portion 115 with two generally perpendicular or circumferentially extending transitions. This undulating portion 115 provides desired flexibility to the stent 120. The long and short first peaks 111, 116 alternate around the circumference of each ring 130 such that each undulating portion 115 is adjacent one long first peak 111 and one short first peak 116 and further, is embedded or nested within a width or longitudinal length of a ring 130. With the undulating portion 115 imbedded in the ring width, the stent maintains optimum compressibility for delivery within vasculature.

The stent typically is made from a metal alloy such as stainless steel, titanium, nickel-titanium (NiTi or nitinol of the shape memory or superelastic types), tantalum, cobalt-chromium, cobalt-chromium-vanadium, cobalt-chromium-tungsten, gold, silver, platinum, platinum-iridium or any combination of the foregoing metals and metal alloys. However, it is contemplated that the stent may be made from any material and fabricated by any process known in the art.

Turning now to FIGS. 4A-E, there is depicted alternative embodiments of stent ring designs. It is contemplated that any of the designs may be incorporated into the stent of the present invention.

Figure 4A:
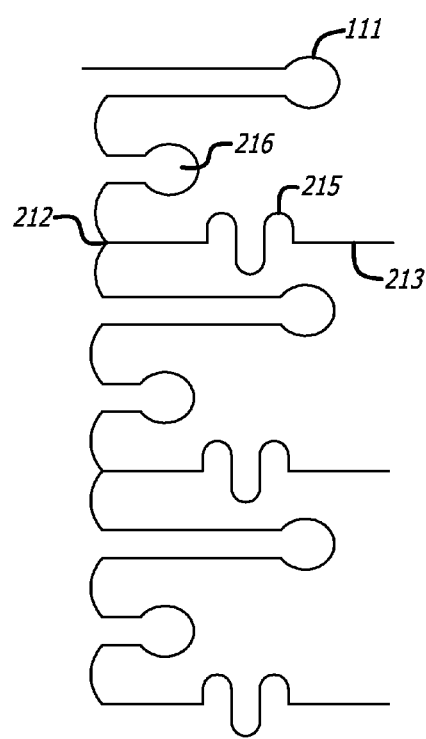
FIG. 4A is a schematic view of a preferred embodiment of the ring design of the present invention in which struts defining one first peak adjacent to each undulating link are shortened.

FIG. 4A depicts a preferred embodiment of a ring design in which one of the first peaks 216 adjacent to each link 213 undulating portion 215 is shorter than the other first peak 211 adjacent the same undulating portion 215. Note that the number of generally perpendicular or circumferential transitions in the undulating portion 215 is reduced to two from the three transitions in the prior art ring design shown in FIGS. 1 and 2. When the stent is compressed for delivery, the undulating portion 215 occupies the space created by the shortened first peak 216, thereby allowing greater compression.

Figure 4B:
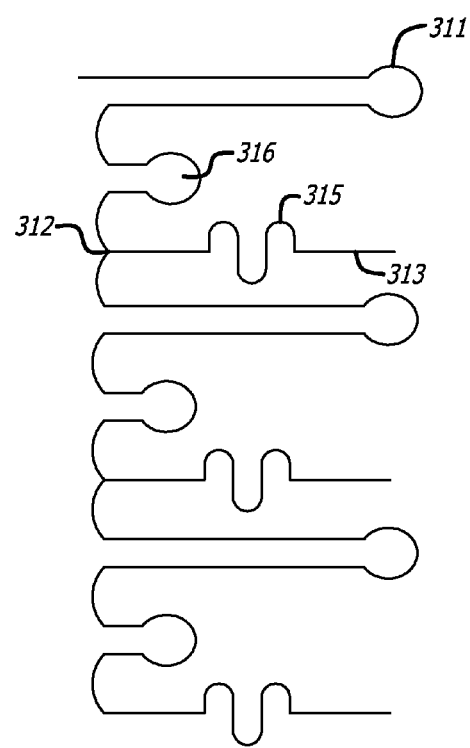
FIG. 4B is a schematic view of an embodiment of the ring design of the present invention in which struts defining one first peak adjacent to each undulating link are shortened and the other first peak adjacent to each undulating link embody relatively longer struts.

FIG. 4B depicts an alternate embodiment of a ring design in which one of the first peaks 316 adjacent to each undulating portion 315 is shorter than the other first peak 311 adjacent the same undulating portion 315, the other first peak 311 being longer than corresponding structures of the prior art design shown in FIGS. 1 and 2. The lengthened first peak 311 provides additional space to accommodate the undulating portion 315 when the stent is compressed for delivery.

FIG. 4C depicts another alternate embodiment of the ring design incorporating the shortened first peaks 416, lengthened first peaks 411, and undulating portions 415 having three generally perpendicular or circumferential transitions. By sacrificing some of the compressibility of the embodiment shown in FIG. 4B, additional flexibility is gained by the additional generally perpendicular transitions of the undulating portions 415.

FIG. 4D depicts another alternate embodiment of the ring design incorporating the shortened first peaks 516, lengthened first peaks 511, and undulating portions 515 having non-symmetrical generally perpendicular or circumferential transitions. By sacrificing some of the compressibility of the embodiment shown in FIG. 4C, additional vessel coverage and flexibility is gained by the larger perpendicular transitions of the undulating portions 515.

Figure 4E:
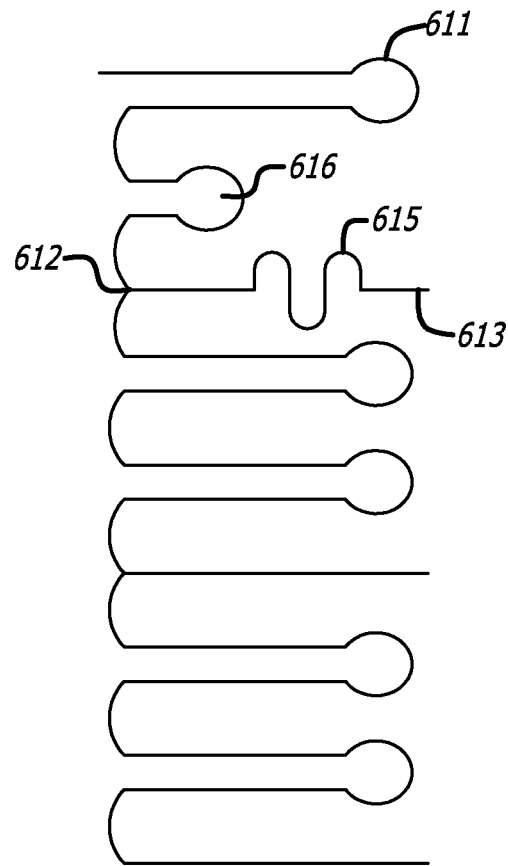
FIG. 4E is a schematic view of an embodiment of the ring design of the present invention in which not all links have an undulating portion.

FIG. 4E depicts yet another alternate embodiment of the ring design in which not all the links 613 have undulating portions 615 and adjacent short first links 616. The first peaks 611 adjacent links without undulating portions 613 are not shortened.

It is contemplated that the number of first and second peaks per ring may be varied depending upon the application and the type of vessel to be treated. The stent of the present invention may contain separate sections, each section having a different ring design chosen for the particular requirements of the vessel in which it is implanted. The peaks are spaced on the rings in such a fashion as to provide uniformity after final expansion inside the vessel.

It is also contemplated any number of links may be provided between second peaks of each ring. Each of the rings can have at least one second peak connected to a link. Longer links may be provided, as well as links of different shapes, as a way of increasing the expandability and diameter of the rings.

Additionally, the stent may have rings and links with variable thickness or variable width struts in order to customize the radial strength of the stent 120, provide higher radiopacity under fluoroscopy, and vary flexibility. The portions where the stent 120 has the thinnest struts will be the most flexible. Variable thickness struts or variable width struts may be more radiopaque and may be positioned along the stent to help the physician position the stent during delivery and implantation in the vessel.

While particular forms of the invention have been illustrated and described, it will be apparent to those skilled in the art that various modifications can be made without departing from the scope of the invention. Accordingly, it is not intended that the invention be limited except by the appended claims.

What is claimed:

1. A stent, comprising:
   a cylindrical body having a plurality of rings aligned along a common longitudinal axis, the rings having a first delivery diameter and a second implanted diameter, the rings including struts defining a plurality of first peaks directed in a first longitudinal direction and a plurality of second peaks directed in a second, opposite longitudinal direction;
   at least one link connecting a second peak of one ring with a second peak of another ring and having an undulating portion; and
   each link being located between a short first peak and a long first peak, the short first peak having struts defining a shorter longitudinal length than the long first peak to provide a space for the undulating portion, wherein at least one long first peak aligns with a second peak of an adjacent ring which is attached to a link.

2. The stent of claim 1, wherein each ring has a plurality of long first peaks, each long first peak being aligned with a second peak of an adjacent ring which is attached to a link.

3. The stent of claim 1, wherein each ring has six second peaks and six first peaks, three of the first peaks defining short first peaks and three of the first peaks defining long first peaks, the short first peaks and long first peaks being spaced in an alternating pattern around a circumference of the ring.

4. The stent of claim 3, wherein the first peaks and second peaks of longitudinally adjacent rings are configured such that only three second peaks of adjacent rings are aligned.

5. The stent of claim 1, wherein each link has two circumferentially extending transitions.

6. The stent of claim 1, wherein each link has three circumferentially extending transitions.

7. The stent of claim 1, each link further comprising transitions extending generally perpendicular to a longitudinal axis of the stent, the perpendicular transitions having a long portion directed towards an adjacent short first peak and a relatively shorter portion directed towards an adjacent long first peak.

8. The stent of claim 1, wherein each ring has a plurality of second peaks and each of the plurality of second peaks are connected by links.

9. The stent of claim 1, wherein all links have undulating portions.

10. The stent of claim 1, wherein each link is attached only to second peaks of each ring.

11. The stent of claim 1, wherein of the plurality of peaks only those second peaks of adjacent rings which are connected by a link are in phase when the rings are in the first delivery position.

12. A stent, comprising:

a cylindrical body having a plurality of rings aligned along a common longitudinal axis, the rings having a first delivery diameter and a second implanted diameter, the rings including struts defining a plurality of first peaks directed in a first longitudinal direction and a plurality of second peaks directed in a second, opposite longitudinal direction;

at least one link connecting a second peak of one ring with a second peak of another ring and having an undulating portion;

at least one straight link connecting a second peak of one ring with a second peak of another ring; wherein at least one first peak adjacent each link with an undulating portion has a shorter longitudinal length than another first peak adjacent the link with the undulating portion to thereby provide a space for the undulating portion when the cylindrical body is in its first delivery diameter and a plurality of first peaks on each ring have the same longitudinal length.

* * * * *